(12) United States Patent
Miki et al.

(10) Patent No.: US 6,503,464 B1
(45) Date of Patent: Jan. 7, 2003

(54) ULTRAVIOLET PROCESSING APPARATUS AND ULTRAVIOLET PROCESSING METHOD

(75) Inventors: Nobuhiro Miki, Tokyo (JP); Takahisa Nitta, Tokyo (JP)

(73) Assignee: Sipec Corporation, Tokyo (JP)

( * ) Notice: Subject to any disclaimer, the term of this patent is extended or adjusted under 35 U.S.C. 154(b) by 0 days.

(21) Appl. No.: 09/416,415

(22) Filed: Oct. 12, 1999

(30) Foreign Application Priority Data

Aug. 12, 1999 (JP) .......................................... 11-228920
Oct. 12, 1999 (JP) .......................................... 11-290248

(51) Int. Cl.⁷ ................................................. B01J 19/08
(52) U.S. Cl. ................................................. 422/186.3
(58) Field of Search ................................... 422/186.3

(56) References Cited

U.S. PATENT DOCUMENTS 6,228,332 B1 * 5/2001 Dunn et al. ............... 422/186.3

FOREIGN PATENT DOCUMENTS

| JP | 62-126638 | 6/1987 |
| JP | 4-369222 | 12/1992 |
| JP | 7-161672 | 6/1995 |

* cited by examiner

*Primary Examiner*—Kishor Mayekar
(74) *Attorney, Agent, or Firm*—Connolly Bove Lodge & Hutz LLP (57) ABSTRACT

An ultraviolet light reaction system is constructed for surface cleaning/surface processing, a processing speed and an apparatus size that can not be attained by any conventional chemical reaction system, are realized, and realization of a time-sharing performance/a high-throughput performance/a compact size is intended. Using an excimer ultraviolet lamp whose light source is excimer ultraviolet rays of a wavelength that transmissive distances to air, gas, and water are 2 mm or more, respectively, surface processing (such as a surface cleaning process) of a substrate disposed in a one-by-one substrate chamber is preformed.

8 Claims, 2 Drawing Sheets

ULTRAVIOLET PROCESSING APPARATUS AND ULTRAVIOLET PROCESSING METHOD

BACKGROUND OF THE INVENTION

1. Field of the Invention

The present invention relates to an ultraviolet processing apparatus used in various processes in manufacturing a semiconductor device or a liquid crystal display device.

2. Description of the Related Art

In manufacturing processes of semiconductor devices or liquid crystal display devices, currently used are surface cleaning apparatus/purification apparatus performing chemical processes for purification of substrates and minutely processed surfaces, and purification of atmosphere and gas to be supplied to processes.

Techniques and systems as described below have been developed and submitted for purification of substrate/device surface, and purification of atmosphere and gas.

1. Wet cleaning system using ozone water

As part of a process in which a one-by-one wafer cleaning apparatus is used, and various liquid chemicals are flowed down on spinning surfaces to remove metal contamination/particle contamination, "ozone water cleaning system" has been developed in which ozone water supplied from an ozone water supply apparatus is flowed down to remove organic matter contamination (see Japanese Patent Application Laid-Open No. 161672/1995).

2. Dry cleaning system and photoresist removal system by UV/ozone method "UV/ozone cleaning system" uses a low-pressure mercury lamp as a light source, and removes organic matter contamination of a surface in generation/decomposition of ozone by ultraviolet rays of wavelengths of 253.7 nm and 184.9 nm and by strong oxidation of atomic active oxygen (see Japanese Patent Application Laid-open No. 369222/1992). Besides, a removal technique of photoresist has been presented in which ultraviolet rays are applied in a highly-concentrated ozone atmosphere in combination with an ozone generator.

3. Gas purification system by catalyst or adsorbent-filled column.

For removing impurities, e.g., water and organic matters in atmospheric gas (such as nitrogen/argon/helium)/material gas (such as oxygen/hydrogen) to be supplied to a process apparatus, processing by a filled column with a catalyst or adsorbent is known.

4. A technique has been presented in which purification processing of semiconductor substrates is performed by generating active matters in a gas phase with excimer laser ultraviolet rays (see Japanese Patent Application Laid-open No. 126638/1987).

The above systems can not have the cluster performance, high throughput performance, and time-sharing performance required for future processing apparatus for the below reasons. That is, for changing from a conventional large-capacity batch processing apparatus to a small-sized one-by-one processing apparatus, disposing to each processing apparatus as cluster, and processing with directly connecting to the processing apparatus, the same throughput as the processing apparatus is required. For this, processing steps must be time-shared in a unit of second.

(1) The conventional wet cleaning system using the ozone water supply apparatus must be provided with a large number of apparatus and so increases in size and is not a cluster apparatus. Anyway, a combination of a silent-discharge type or electrolysis type ozone generator and a diaphragm type or absorption type ozone dissolution apparatus is indispensable.

Since ozone is continuously generated and it can not be time-shared, an ozone decomposition apparatus is indispensable for processing a large quantity of surplus ozone. In case of electrolysis type, a decomposition and removal apparatus for hydrogen generated at the same time must be accompanied. The ozone dissolution apparatus has need of a pressure controller for ozone gas in either case of diaphragm type and absorption type.

(2) The low-pressure mercury lamp used in the UV/ozone method dry cleaning system is a continuous luminescence type light source, and a system with high throughput by a time-sharing process can not be constructed.

(3) In the gas purification system by the filled column with a catalyst or adsorbent, deterioration of performance of the catalyst or adsorbent with time elapsing can not be avoided, and it lacks in reliability of always maintaining the purity.

(4) The excimer laser generator is not easy in its construction and handling. Laser lights are not always required for photochemical reactions for surface cleaning. In this case, an excimer ultraviolet lamp is proper.

In semiconductor/liquid crystal manufacturing processes, progress of each process apparatus is requested in directions that the installation area is as small as possible, the processing speed is as fast as possible, the reliability of processing is as high as possible, and they are connected in a cluster fashion to each other and there is no contamination due to conveyance. For this reason, an apparatus for surface cleaning/surface processing also must be changed from conventional batch type into one-by-one type and a cluster apparatus directly connected to a process apparatus.

At this time, the "processing speed and apparatus size" of the apparatus must be the same as those of the other process apparatus.

SUMMARY OF THE INVENTION

Accordingly, it is an object of the present invention to provide an ultraviolet processing apparatus and an ultraviolet processing method in which an ultraviolet light reaction system is constructed for surface cleaning/surface processing, and "processing speed and apparatus size" that can not be attained by any conventional chemical reaction system, is realized. That is, it is to realize time-sharing performance/high-throughput performance/compact size.

In order to attain the above object, an ultraviolet processing apparatus according to the present invention is used for purification of a surface and a material in relation to manufacturing a semiconductor device or a liquid crystal display device, and comprises, as a light source, an ultraviolet lamp for applying ultraviolet rays of a wavelength that 50% transmissive distances to air, water, steam, and a gas are 2 mm or more, respectively.

According to an aspect of the ultraviolet processing apparatus of the present invention, said surface is one selected from among process surfaces from a substrate to a semiconductor device, surfaces of process apparatus and process apparatus parts, and surfaces of apparatus and apparatus parts in relation to lithographic processes.

According to an aspect of the ultraviolet processing apparatus of the present invention, said material is one selected from among raw water, pure water, drain, air, general gases, and special material gases. Here, as examples of the general gases and special material gases, listed are $N_2$, $O_2$, and $CO_2$ as the general gases, and $H_2$, He, $B_2H_6$, and $SiO_4$ as the special material gases.

According to an aspect of the ultraviolet processing apparatus of the present invention, said ultraviolet lamp is an excimer ultraviolet lamp.

According to an aspect of the ultraviolet processing apparatus of the present invention, it is disposed in a surface purification apparatus using steam, and a surface being processed with steam is irradiated with ultraviolet rays that 50% transmissive distance to steam is 2 mm or more, in a superimposition manner with steam.

According to an aspect of the ultraviolet processing apparatus of the present invention, it is disposed in a one-by-one surface purification apparatus, and a surface being processed with steam is irradiated with ultraviolet rays that 50% transmissive distance to steam is 2 mm or more, in a superimposition manner with steam to remove organic matters and adhering particles.

According to an aspect of the ultraviolet processing apparatus of the present invention, it is disposed in a one-by-one surface purification apparatus, and a surface being cleaned with ultrapure water or a liquid chemical is irradiated with ultraviolet rays that 50% transmissive distance to air is 2 mm or more, to perform a radical reaction process.

According to an aspect of the ultraviolet processing apparatus of the present invention, it is disposed in a resist removal apparatus used in a lithographic process, and a surface being processed with steam is irradiated with ultraviolet rays to remove a resist.

According to an aspect of the ultraviolet processing apparatus of the present invention, it is constructed by comprising an ultraviolet lamp for applying ultraviolet rays of a wavelength that transmissive distance to water is 2 mm or more, a quartz double tube surrounding said ultraviolet lamp, and a light reflection tube surrounding said ultraviolet lamp through said quartz double tube, and pure water dissolving oxygen is supplied inside said quartz double tube to change pure water into ozone water by a photochemical reaction.

According to an aspect of the ultraviolet processing apparatus of the present invention, it is constructed by comprising an ultraviolet lamp for applying ultraviolet rays of a wavelength that transmissive distance to water is 2 mm or more, a quartz double tube surrounding said ultraviolet lamp, and a light reflection tube surrounding said ultraviolet lamp through said quartz double tube, and raw water is supplied inside said quartz double tube to purify raw water by a photochemical reaction.

According to an aspect of the ultraviolet processing apparatus of the present invention, it is constructed by comprising an ultraviolet lamp for applying ultraviolet rays of a wavelength that transmissive distance to water is 2 mm or more, a quartz double tube surrounding said ultraviolet lamp, and a light reflection tube surrounding said ultraviolet lamp through said quartz double tube, and drain containing organic matters is supplied inside said quartz double tube to purify drain by a photochemical reaction.

According to an aspect of the ultraviolet processing apparatus of the present invention, it is constructed by comprising an ultraviolet lamp for applying ultraviolet rays of a wavelength that transmissive distance to air is 2 mm or more, a quartz double tube surrounding said ultraviolet lamp, and a light reflection tube surrounding said ultraviolet lamp through said quartz double tube, and air or air to which oxygen is added is supplied inside said quartz double tube to change oxygen into ozone by a photochemical reaction.

According to an aspect of the ultraviolet processing apparatus of the present invention, it is constructed by comprising an ultraviolet lamp for applying ultraviolet rays of a wavelength that transmissive distance to air is 2 mm or more, a quartz double tube surrounding said ultraviolet lamp, and a light reflection tube surrounding said ultraviolet lamp through said quartz double tube, and atmospheric air is supplied inside said quartz double tube to purify atmospheric air by a photochemical reaction.

According to an aspect of the ultraviolet processing apparatus of the present invention, it is constructed by comprising an ultraviolet lamp for applying ultraviolet rays of a wavelength that transmissive distance to each gas is 2 mm or more, a quartz double tube surrounding said ultraviolet lamp, and a light reflection tube surrounding said ultraviolet lamp through said quartz double tube, and a general gas or a special material gas is supplied inside said quartz double tube to purify contaminative components in said gas by a photochemical reaction.

According to an aspect of the ultraviolet processing apparatus of the present invention, a gas having no absorption at the ultraviolet lamp wavelength is sealed or flowed in a space portion between said ultraviolet lamp and said quartz double tube, and a space portion between said quartz double tube and said light reflection tube.

An ultraviolet processing method according to the present invention is a method used for purification of a surface and a material in relation to manufacturing a semiconductor device or a liquid crystal display device, wherein an ultraviolet lamp for applying ultraviolet rays of a wavelength that 50% transmissive distances to air, water, steam, and a gas are 2 mm or more, respectively, is used as a light source.

According to an aspect of the ultraviolet processing method of the present invention, said surface is one selected from among process surfaces from a substrate to a semiconductor device, surfaces of process apparatus and process apparatus parts, and surfaces of apparatus and apparatus parts in relation to lithographic processes.

According to an aspect of the ultraviolet processing method of the present invention, said material is one selected from among raw water, pure water, drain, air, general gases, and special material gases.

According to an aspect of the ultraviolet processing method of the present invention, it is used for surface purification using steam, and a surface being processed with steam is irradiated with ultraviolet rays that 50% transmissive distance to steam is 2 mm or more, in a superimposition manner with steam.

According to an aspect of the ultraviolet processing method of the present invention, a one-by-one surface purification apparatus is used, and a surface being processed with steam is irradiated with ultraviolet rays that 50% transmissive distance to steam is 2 mm or more, in a superimposition manner with steam to remove organic matters and adhering particles.

According to an aspect of the ultraviolet processing method of the present invention, a one-by-one surface purification apparatus is used, and a surface being cleaned with ultrapure water or a liquid chemical is irradiated with ultraviolet rays that 50% transmissive distance to air is 2 mm or more, to perform a radical reaction process.

According to an aspect of the ultraviolet processing method of the present invention, a resist removal apparatus used in a lithographic process is used, and a steam-processed surface is irradiated to remove a resist.

DETAILED DESCRIPTION OF THE PREFERRED EMBODIMENTS

Hereinafter, concrete embodiments of the present invention will be described.

The most important matter for attaining the object of the present invention is unerring selection of ultraviolet lamp. In particular, selections of the ultraviolet wavelength and time characteristics of a lamp used in an ultraviolet reactor are important technical factors. The present inventors variously examine the problems in the conventional ultraviolet application techniques, and perceive the following points as new issues:

1. selection of ultraviolet wavelength characteristics;
2. selection of time response of ultraviolet lamp; and
3. making ultraviolet irradiation light quantity highly efficient.

1. Selection of Ultraviolet Wavelength Range

The shorter the ultraviolet wavelength is, the greater the energy is and the lower the transmissivity to the irradiation atmosphere is. The ultraviolet wavelength must be so selected as to satisfy the transmissivity. The present inventors have stored up transmittance data of ultraviolet rays to air/water/steam, and investigated photochemical reactions by studying for many years to obtain an index for wavelength range selection.

The below Table 1 shows relations between ultraviolet wavelengths and 50% transmissive distances to air/water/steam. It is found that ultraviolet wavelengths whose 50% transmissive distances are 10 mm or more in steam atmosphere, are 185 nm or more.

A relation between the light absorption sectional area of molecules present in the atmosphere and the light transmissivity, is given by expression (1). Logarithms of the transmissivity become proportional to distances. The inventors use 50% transmissive distance as an index. This 50% transmissive distance is given by expression (2). Table 1 shows relations between ultraviolet wavelengths and 50% transmissive distances to air, water, and steam obtained by expression (2) or actual measurements. For example, the 50% transmissive distance of ultraviolet rays of the wavelength of 172 nm to air is obtained as 3.1 mm from the light absorption sectional area of oxygen ($0.259 \times 10^{-19}$ molecules/cm$^2$) while the actual measurement of 2.2 mm is obtained. Both are almost equal.

$$\delta CL = \ln(I^0/I) \quad (1)$$

$\delta$: light absorption sectional area (molecules/cm$^2$), $O_2$... $0.259 \times 10^{-19}$ C: molecule concentration (partial pressure of molecule)

L: transmissive distance (cm)

$I^0/I$: light transmissivity=incident light intensity/transmitted light intensity (2)

$$\delta CL_{50} = \ln(100/50)$$

$L_{50}$: 50% transmissive distance

Therefore, 50% transmissive distance means the distance that the light intensity becomes half because of light absorption by air, water, steam or gas. More specifically from the expressions, 50% transmissive distance is given by:

$$L_{50} = (1/\delta \cdot C) \ln(100/50).$$

From Table 1, it is found that excimer ultraviolet lamps in the wavelength range that the distance at which the transmittance to water is attenuated to 50% is 1 mm or less is unsuited for irradiation in water, and can not be applied to a wet surface processing apparatus.

An excimer ultraviolet lamp of the wavelength range of 190 nm can sufficiently be applied because the water transmittance 50% distance is scores mm.

As for an excimer ultraviolet lamp of the wavelength range of 170 nm, although the transmittance to air is severe as several mm, it can be applied to a dry surface processing apparatus to operate in air if the irradiation distance is used to be close. If an excimer ultraviolet lamp of the wavelength range of 190 nm is used, the transmissive distance in air can be obtained enough.

For the purification object for gas not showing the ultraviolet absorption action, such as $N_2$, $H_2$, He, Ar, and Xe, it is found that excimer ultraviolet lamps of the wavelength range of 170 nm or the wavelength range less than it also can be applied without any restriction by irradiation distance.

From the above consideration, it is found that excimer ultraviolet rays of a wavelength that the transmissive distances to air, water, and steam are 2 mm or more, respectively, is suitable.

Although they are omitted in Table 1, the below excimer ultraviolet lamps can be applied to water, air, and gas not having ultraviolet absorption, without any restriction by irradiation distance. Each Wavelength is shown in parentheses.

KrF (248 nm), XeI (253 nm), $Cl_2$ (258 nm), XeBr (282 nm), $Br_2$ (291 nm), XeCl (308 nm), $I_2$ (341 nm), and XeF (351 nm)

TABLE 1

Ultraviolet Wavelength and 50% Transmissive distances to Air/Water/Steam

| excimer ultraviolet lamp | wave-length nm | energy eV | 50% transmissive distance | | |
|---|---|---|---|---|---|
| | | | air mm | water mm | steam mm |
| Xe excimer lamp | 172 | 7.21 | 3 | | |
| ArCl excimer lamp | 175 | 7.08 | 6 | <10 | <10 |
| | 185 | 6.70 | 40 | 10 | >1 × 10$^4$ |
| KrI excimer lamp | 191 | 6.49 | 100 | 28 | |
| ArF excimer lamp | 193 | 6.42 | >100 | 42 | |
| KrBr excimer lamp | 207 | 5.99 | | >100 | |
| KrCl excimer lamp | 222 | 5.58 | | | |
| low-pressure mercury lamp | 185 · 254 | | | | |
| i-line lamp | 365 | 3.41 | | | |

Table 2 shows energies of wavelengths of excimer ultraviolet rays and typical examples of photochemical reactions.

From Table 2, it is found that, since an excimer ultraviolet lamp in the wavelength range of 190 nm or less generates H.OH radical by irradiation of water, strong reaction medium is obtained. Besides, it is found that an excimer ultraviolet lamp in the wavelength range of 200 nm or less generates ozone by oxygen dissociating into oxygen atoms by irradiation of air, and a strong oxygen atmosphere is obtained. Although a light of a longer wavelength range than 200 nm also has an O3 generation reaction, various conditions participate and the quantum efficiency of the photochemical reaction is low, besides, it is found that O3 generation is instable.

Although the details are not shown in Table 2, hydrocarbons generally have large absorption sectional area in the whole of the wavelength range of 130 nm to 200 nm. For purification object for atmospheric gas/material gas such as N2, H2, He, Ar, and Xe, this whole wavelength range can be applied. It is found that the shorter the wavelength is, the larger the reactivity is and the more the effectiveness is.

TABLE 2

Energies of Wavelengths of Excimer Ultraviolet Rays and Photochemical Reactions

| wavelength mm | photochemical reaction of water | photochemical reaction of oxygen | photochemical reaction of hydrocarbon |
|---|---|---|---|
| 135 (9.19 eV) | ↕ | ↕ | ↕ |
| | $H_2O + h\nu = H_2 + O(^1D_2)$ | $O_2 + h\nu = O(^3P) + O(^1D_2)$ | |
| | | $O_2 + O + M \rightarrow O_3 + M$ | |
| | ↓ | ↓ | |
| 175 (7.08 eV) | ↕ | ↕ | |
| | $H_2O + h\nu = H + OH(X^2\Pi)$ | $O_2 + h\nu = 2O(^3P)$ | hydrocarbon + $h\nu = H_2O + CO_2$ |
| | | $O_2 + O + M \rightarrow O_3 + M$ | |
| | ↓ | ↓ | |
| 190 (6.49 eV) | ↓ | | |
| 203 (6.49 eV) | | ↓ | ↓ |

2. Selection of Time Response of Ultraviolet Lamp

An ultraviolet lamp is selected in accordance with which of a moment type and a constant type ultraviolet processing is performed in.

Moment Type Lamp

An ultraviolet excimer lamp can be used in a moment type process. It reaches its stationary state in several seconds after being lit. The irradiation light quantity in the non-stationary period for that several seconds differs merely by only several percents from that in a stationary period. If the lamp temperature is kept at a constant temperature, this several percents can be further reduced. According to selection of an excimer ultraviolet lamp, a cleaning step of performing surface organic matter removal by ultraviolet irradiation for ten seconds, for example, can be constructed. An ultraviolet excimer lamp is suitable for a sequential process in a unit time of second in one-by-one type ultraviolet processing.

Constant Type Lamp

In ultraviolet lamps, mercury lamps, deuterium lamps, halogen lamps, etc., the necessary time from lighting to the stationary luminescence is long. For example, a low-pressure mercury lamp requires about thirty minutes to reach its stationary state. Since it is stable after reaching the stationary state, it is suitable for a constant type process.

3. Making Ultraviolet Irradiation Light Quantity Highly Efficient (High Light-Efficiency for Realizing Compact Size)

An ultraviolet light is radiated from a light source to all directions. A light condensation technique on a surface to be processed is a key of a highly efficient utilization of the light quantity. The present inventors have developed the following means and attained a complete utilization of irradiation light quantity.

An excimer ultraviolet lamp is inserted in the interior of an outer tube whose inner surface is a reflection surface. A quartz double tube is disposed in the space between the outer tube and the excimer ultraviolet lamp. A gas or liquid is flowed in this tube. Thereby, with no light quantity loss except a little absorption loss by the quartz double tube wall, it was realized to irradiate the gas or liquid with ultraviolet energy at a high absorption efficiency.

By combining the development means as mentioned above, various kinds of excimer ultraviolet processing apparatus can be constructed.

Figure 1:
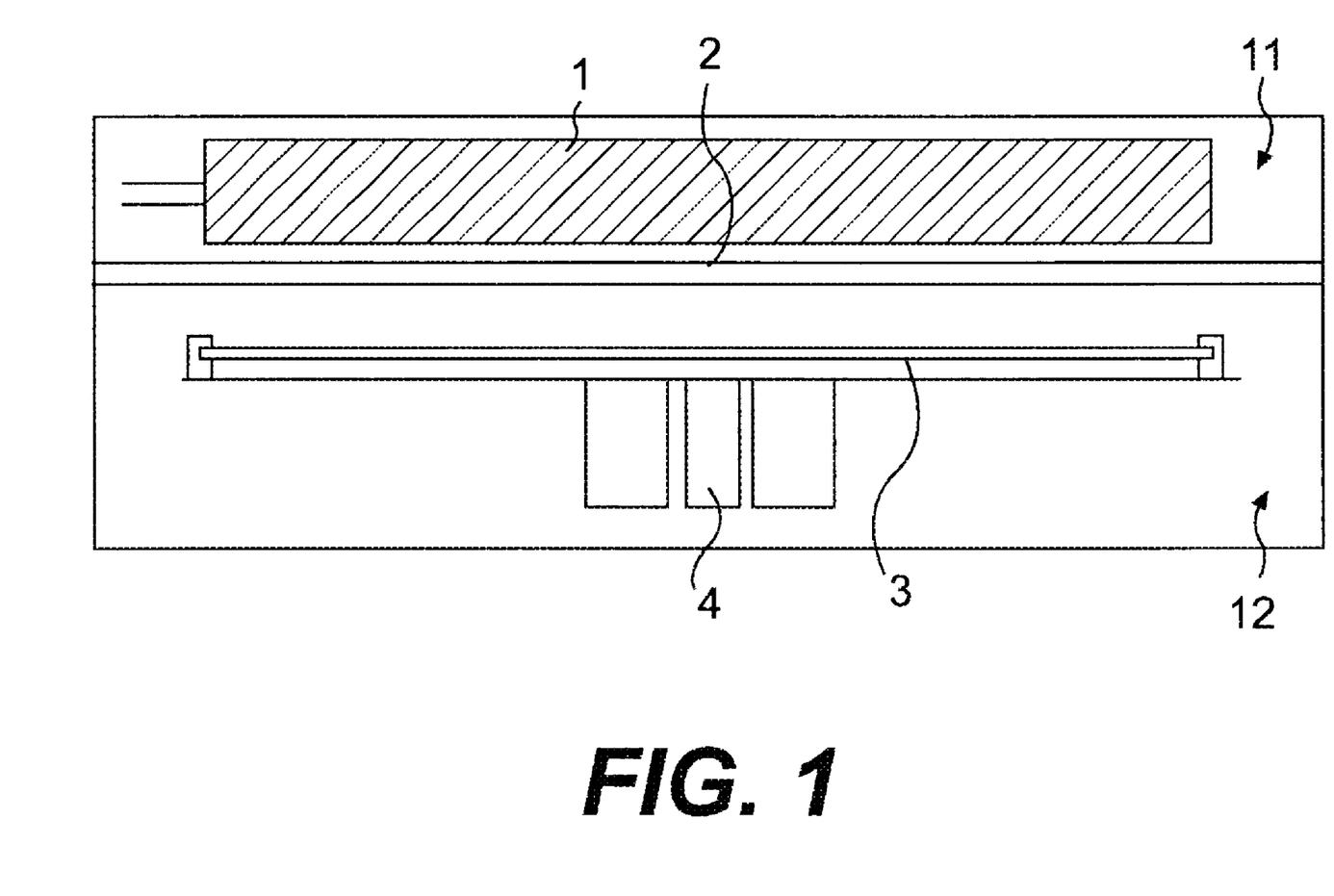
FIG. 1 is a fundamental view showing a principal construction of an excimer ultraviolet processing apparatus disposed in a one-by-one surface processing apparatus.

FIG. 1 shows a fundamental view of an excimer ultraviolet processing apparatus disposed in a one-by-one surface processing apparatus.

This excimer ultraviolet processing apparatus is constructed by comprising a lamp chamber 11 including an excimer ultraviolet lamp 1, a substrate chamber 12 including a spin rotation system 4 in which a substrate 3 is disposed so as to be opposite to the excimer ultraviolet lamp 1, and a quartz window board 2 provided between the excimer ultraviolet lamp 1 and the substrate 3.

The substrate 3 receives ultraviolet irradiation from the excimer ultraviolet lamp 1 with spinning or moving horizontally by the spin rotation system 4. Although they are omitted in FIG. 1, the substrate chamber 12 is accompanied with a gate valve for taking substrate in/out and equipment for changing atmosphere, discharging gas and discharging water. In case of dry processing only, the quartz window board 2 can be omitted. In case of performing removal of photoresist in a photolithographic process, an inlet for ozone may be disposed. In case of wet processing, a nozzle for flowing down ultrapure water/liquid chemical onto a substrate surface, and a high-frequency supersonic oscillator at need are disposed.

Figure 2:
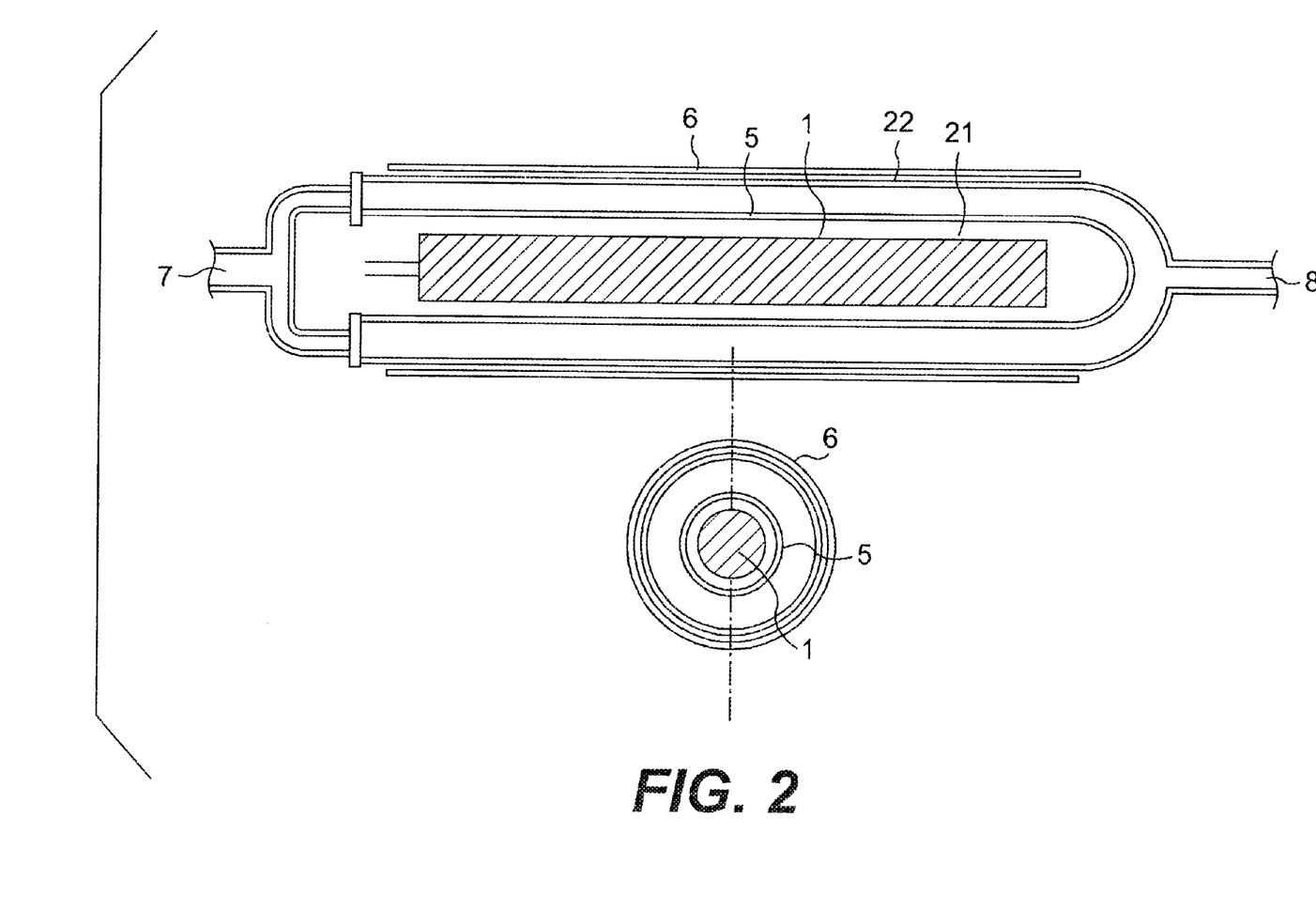
FIG. 2 are fundamental views (cross-sectional views and vertically sectional views) showing a principal construction of an excimer ultraviolet total reflection type apparatus.

FIG. 2 show fundamental views of an excimer ultraviolet total reflection type apparatus.

This apparatus is constructed by comprising an excimer ultraviolet lamp 1, a quartz glass double tube 5 surrounding the excimer ultraviolet lamp 1, and a light reflection tube 6 which surrounds the excimer ultraviolet lamp 1 through the quartz glass double tube 5 and whose inner surface is a reflection surface. As the reflection surface of the light reflection tube 6, usable are metallic aluminum, alumina ceramics, etc., of mirror surface. Water, gas, atmosphere, and others to be processed are introduced into the quartz glass double tube 5, and ultraviolet rays are applied by the excimer ultraviolet lamp 1. In the drawings, 7 shows an inlet, 8 shows an outlet. The lamp capacity and the double tube shape are designed in accordance with the processing object.

In the space portion 21 between the excimer ultraviolet lamp 1 and the quartz double tube 5 and the space portion 22 between the quartz double tube 5 and the light reflection tube 6, a gas having no absorption at the ultraviolet lamp wavelength is sealed or flowed as occasion demands to prevent ultraviolet absorption loss due to air and deterioration of an outer electrode of the excimer ultraviolet lamp 1. As the above gas, usable is an inert gas such as nitrogen, helium, or argon. Gas flow is used also for the object of cooling when the light quantity of the excimer ultraviolet lamp 1 is great.

Embodiments of the invention using the above apparatus will be described in detail with reference to the respective examples.

EXAMPLE 1

For processing of purification of substrates and minutely processed surfaces, and purification of atmospheric gas/material gas to be supplied to a process apparatus, etc., in a manufacturing process of a semiconductor or a liquid crystal display device, excimer ultraviolet lamps used by being incorporated in an excimer ultraviolet reactor, and their performances were investigated. The results are exemplified in Table 3.

Irradiation light quantity is shown by light quantity per each lamp surface. In case that lamps are arranged at intervals of almost lamp diameter in parallel with a surface to be processed and reflecting plates are provided on the rear surfaces in radiation directions of the lamps, unless the distance between the lamps and the surface to be processed is extremely great, the light quantity per quartz tube surface and the light quantity per surface to be processed of the lamps are almost the same quantity.

As examples of organic compound decomposition reaction, shown are results of evaluating photolysis time (90% decomposition time) of oleic acid. When the transmittance conditions to air/water are satisfied, it is apparent that the shorter the wavelength of excimer ultraviolet rays used is, the greater the reaction speed is.

TABLE 3

Kinds of Excimer Ultraviolet Lamps and Their Reaction Performances

| excimer | wavelength nm | energy eV | irradiation light quantity mJ/cm$^2$ | oleic acid decomposition time (90% decomposition) sec |
|---|---|---|---|---|
| Xe | 172 | 7.21 | 20 | 250 |
| ArCl | 175 | 7.08 | 20 | 260 |
| KrI | 191 | 6.49 | 20 | 310 |
| ArF | 193 | 6.42 | 20 | 320 |
| KrBr | 207 | 5.99 | 20 | 360 |
| KrCl | 222 | 5.58 | 20 | 450 |

Notes: oleic acid quantity on surface: 0.02 mg/cm$^2$, 0.4 × 10$^{17}$ molecules/cm$^2$, (thickness of oleic acid layer of about 0.2 μm)

EXAMPLE 2

Investigated was the effect of means of superimposing steam-processed surfaces with ultraviolet irradiation that 50% transmissive distance to steam is 2 mm or more.

Table 4 shows purification test results of oleic acid adhering to silicon wafer surfaces. After saturated steam at 120° C. is sprayed for thirty seconds, oleic acid was purified to monomolecular layer or less.

In case of superimposing ultraviolet irradiation on 120° C. saturated steam processing, it was removed to monomolecular layer ten seconds after, and to less than the detection limit of FTIR measurement twenty seconds after.

TABLE 4

Steam Processing and Steam/Ultraviolet Rays Superimposition Processing of Silicon Wafer Surface-Adhering Oleic Acid

| | before processing | 10 sec processing | 30 sec processing |
|---|---|---|---|
| steam processing [120° C. saturated steam] | | | |
| oleic acid-adhering quantity | 0.2 mg/cm$^2$ | 0.5 μg/cm$^2$ | 0.05 μg/cm$^2$ |
| (oleic acid molecules) | 4 × 10$^{17}$/cm$^2$ | 1 × 10$^{15}$/cm$^2$ | 1 × 10$^{14}$/cm$^2$ |
| thickness of molecular layer | about 2700 molecular layers on average | about 7 molecular layers on average | monomolecular layer or less |
| steam/ultraviolet rays superimposition processing [120° C. saturated steam] | | | |
| oleic acid-adhering quantity | 0.2 mg/cm$^2$ | 0.1 μg/cm$^2$ | <0.005 ng/cm$^2$ |
| (oleic acid molecules) | 4 × 10$^{17}$/cm$^2$ | 2 × 10$^{14}$/cm$^2$ | <1 × 10$^{10}$/cm$^2$ |
| thickness of molecular layer | about 2700 molecular layers on average | almost monomolecular layer on average | less than detection limit | silicon wafer: 4 inches
steam-spraying quantity: 2.55 L/sec, line slit nozzle: 50 mm × 1.0 mm
ultraviolet irradiation quantity: KrI excimer lamp 10 mW/cm$^2$ (silicon wafer surface)
detection limit of FTIR/ATR: 1 × 10$^{12}$ molecules/cm$^2$) detection limit

EXAMPLE 3

Shown are examples of excimer ultraviolet reactor disposed in a one-by-one surface cleaning apparatus of spin rotation type or horizontal movement type, wherein an excimer ultraviolet lamp of a water-transmissive distance of several mm or more in parallel with a surface to be processed, and radical reaction processing is performed by irradiating a surface to be cleaned by ultrapure water/liquid chemical.

The excimer ultraviolet processing apparatus shown in FIG. 1 was used, and a KrI excimer ultraviolet lamp (191 nm: irradiation light quantity of 20 mJ/cm$^2$) was used.

In the cleaning step shown in Table 5, one-by-one cleaning of semiconductor substrates was performed.

The cleaning step is a removal step of surface adhesion organic matters. Wafer surfaces are supplied with ultrapure water and irradiated with ultraviolet rays.

The cleaning step is a removal step of metallic impurities and particles. Fluoric acid/hydrogen peroxide mixed with a surface active agent is supplied to perform removal processing.

The cleaning step is a removal step of a surface active agent adsorbed by a surface by processing of. Like step, wafer surfaces are supplied with ultrapure water and irradiated with ultraviolet rays.

Hereinafter, through cleaning step, drying is performed lastly.

By ON/OFF of the excimer ultraviolet lamp, cleaning liquids are switched instantaneously from ultrapure water to ozone water/from ozone water to ultrapure water. That is, processing was possible fully to cope with processing step switching at intervals of second.

Organic matters on wafer surfaces after cleaning are less than 10$^{12}$ molecules/cm$^2$ that is the detection limit of a highly-sensitive reflection FTIR measuring instrument. It was confirmed that the cleaning effect was fully attained.

TABLE 5

One-by-one Wafer Cleaning Conditions

| cleaning step | cleaning liquid | cleaning liquid flow rate | step time |
|---|---|---|---|
| ① excimer ultraviolet cleaning | ultrapure water | 3 L/min | 10 sec |
| ② fluoric acid/hydrogen peroxide cleaning | HF 0.5%/$H_2O_2$ 0.5% | 3 L/min | 10 sec |
| ③ excimer ultraviolet cleaning | ultrapure water | 3 L/min | 10 sec |
| ④ dilututed fluoric acid cleaning | HF 0.2% | 3 L/min | 10 sec |
| ⑤ ultrapure water cleaning | ultrapure water | 3 L/min | 5 sec |

EXAMPLE 4

Shown are examples of excimer ultraviolet reactor disposed in a one-by-one surface dry processing apparatus of spin rotation type or horizontal movement type, wherein an excimer ultraviolet lamp of a wavelength of an air-transmissive distance of several mm or more, concretely 2 mm or more, is disposed in parallel with a surface to be processed, and a surface is irradiated to remove organic substances.

The excimer ultraviolet processing apparatus shown in FIG. 1 was used, a Xe excimer ultraviolet lamp (172 nm: irradiation light quantity of 20 mJ/cm$^2$) was used, and surfaces of silicon wafers having adsorbed a surface active agent were processed. The surface active agent adsorption quantity is about 1.5 ng/cm$^2$ (about $0.5 \times 10^{16}$ molecules/cm$^2$ as octyl amine $CH_3(CH_2)_7NH_2$).

As Table 6 shows the results, the organic matter concentrations on wafer surfaces after thirty seconds of irradiation time is less than the detection limit of the highly-sensitive reflection FTIR measuring instrument. It was confirmed that the surface active agent was completely removed.

TABLE 6

One-by-one Wafer Dry Cleaning Conditions

| excimer ultraviolet lamp | irradiation atmosphere | irradiation distance | irradiation time | surface organic matter concentration |
|---|---|---|---|---|
| Xe excimer lamp | air | 5 mm | 30 sec | less than detection limit <$10^{12}$ molecules/cm$^2$ |

EXAMPLE 5

Shown are examples of excimer ultraviolet processing apparatus for decomposing and removing resist films in air.

An excimer ultraviolet lamp of a wavelength of an air-transmissive distance of several mm or more, concretely 2 mm or more, disposed in a resist removal processing apparatus in a lithographic process, and a surface is irradiated to decompose resist films. The processing apparatus and the excimer ultraviolet lamp are the same as those of Example 3. Resist films could be removed on the irradiation conditions shown in Table 7. In case of using ozone gas flow for promoting resist decomposition reaction, removal was possible in 180 seconds of irradiation time. An ozone generator for ozone gas flow will be described in Example 6.

TABLE 7

Resist Decomposition Removal Conditions

| excimer lamp | irradiation atmosphere | irradiation distance | irradiation time |
|---|---|---|---|
| Xe excimer ultraviolet lamp | air ozone gas flow | 2 mm 2 mm | 30 min 180 sec |

(processed film structure) resist film: positive type DNQ novolac resin 1.0 μm (130° C., 5 min post-baked)
sililation layer: HMDS90S
thermal oxidation film: $SiO_2$ 3000 Å

EXAMPLE 6

Shown is an example of excimer ultraviolet processing apparatus for peeling off resist films by steam/ultraviolet rays superimposition processing. Here, shown is an example of steam/ultraviolet rays superimposition processing for ion-implanted resist films, which are hard to peel off.

Sample: silicon thermal oxidation film etched surface; ion-implantation to the lower-layer silicon substrate
Ion-implantation conditions: acceleration energy of 80 keV; dose amount of phosphorus of $6 \times 10^{15}$/cm$^2$
Ultraviolet lamp: KrI excimer lamp, wavelength of 191 nm
Ultraviolet irradiation quantity: 10 mW/cm$^2$
The below Table 8 shows the peeling-off results.

After 100° C. saturated steam processing and ultraviolet irradiation processing for two minutes of the condition 1, the resist film could be peeled off and removed by spraying process for one minute.

After 120° C. saturated steam processing and ultraviolet irradiation processing for thirty seconds of the condition 2, the resist film could be peeled off and removed by spraying process for thirty seconds.

TABLE 8

Effect of Ultraviolet Irradiation Superimposition for Ion-implanted Resist Removal

| processing step | first step steam-contacting process ultraviolet irradiation superimposition | second step steam-spraying process | resist removal state |
|---|---|---|---|
| condition 1 | | | |
| kind of steam | saturated steam | saturated steam | removed in processing time of 3 min |
| temperature of steam | 100° C. | 100° C. | |
| processing time | 2 min | 1 min | |
| condition 2 | | | |
| kind of steam | saturated steam | superheated steam | removed in processing time of 1 min |
| temperature of steam | 120° C. | 130° C. | |
| processing time | 30 sec | 30 sec | |

EXAMPLE 7

Constructed was an excimer ultraviolet total reflection type ozone water supply apparatus comprising an excimer ultraviolet lamp of a wavelength of a water-transmissive distance of several mm or more, concretely 2 mm or more, a quartz double tube, and a light reflection tube, wherein pure water dissolving oxygen was supplied inside the quartz double tube to change into ozone water by a photochemical reaction.

The excimer ultraviolet total reflection type apparatus shown in FIG. 2 and Table 7 was used, and as the excimer ultraviolet lamp, used was a KrI excimer ultraviolet lamp (191 nm: irradiation light quantity of 20 mJ/cm$^2$) whose in-water 50% transmissive distance is 28 mm. Irradiation light from the lamp is transmitted in pure water. The light transmitted in pure water is totally reflected to return to the pure water side, and a total reflection condition without any loss of irradiation light can be obtained.

Pure water at the normal temperature equilibrium-dissolves oxygen in the air at a concentration of about 7 ppm. In passing through the double tube, this dissolved oxygen is changed into ozone in a moment by the energy of 191 nm wavelength. By changing the irradiation light quantity of the excimer ultraviolet lamp by control of the applied quantity of electricity, the ozone concentration could be controlled within the range of 0 to about 7 ppm. When ozone water at a higher concentration is wanted to supply, pure water at a higher oxygen concentration is supplied.

Besides, the excimer ultraviolet lamp is capable of momentary ON/OFF, and ozone water supply and pure water supply can be arbitrarily switched. At this time, by selecting the size of the double quartz tube and setting the passage time of pure water in the tube to the degree of several seconds, ozone water/pure water switching could be performed in the unit of second.

mance. Besides, because of continuously electrifying type, a decomposition processing apparatus for surplus ozone was needed. Besides, a decomposition removal apparatus for hydrogen, which was generated at the same time by electrolysis, was also needed. In the diaphragm type ozone dissolution apparatus, switching operation between ozone dissolution and dissolution stop was complicated and difficult. Accordingly, momentary ON/OFF in switching and supplying ozone water for one-by-one cleaning was impossible, and a sufficient throughput could not be obtained.

EXAMPLE 8

Constructed was an excimer ultraviolet total reflection type drain purification apparatus comprising an excimer ultraviolet lamp of a wavelength of a water-transmissive distance of several mm or more, concretely 2 mm or more, a quartz double tube, and a light reflection tube, wherein drain containing organic matters was supplied inside the quartz double tube to purify the drain by a photochemical reaction.

The excimer ultraviolet total reflection type apparatus shown in FIG. 2 and Table 10 was used, and as the excimer

TABLE 9

Construction of Ozone Water Supply Apparatus

| | irradiation part | | | passed liquid | |
|---|---|---|---|---|---|
| | diameter mm | length mm | area cm$^2$ | volume cm$^3$ | passed liquid quantity ml/sec | residence time sec |
| [excimer lamp] | 30 | 300 | 280 | | | |
| double quartz flowing part inside diameter | 35 | 300 | | 90 | 50 | 2 |
| double quartz flowing part outside diameter | 40 | 300 | | | | |

Comparative Example

Using an electrolysis type ozone generator (ozone generation quantity of 4 g/hr) and a diaphragm type ozone dissolution apparatus, ozone water supply to a one-by-one cleaning apparatus was performed. Although the necessary quantity of ozone is the degree of 0.4 g/hr, the electrolysis type ozone generator can not be decreased in its perforultraviolet lamp, used was a KrI excimer ultraviolet lamp (wavelength of 191 nm: irradiation light quantity of 20 mJ/cm$^2$) whose in-water 50% transmissive distance is 28 mm. In this apparatus, the ability of decomposing TOC (total organic carbon concentration) in drain to the maximum of 10 ppm was confirmed.

TABLE 10

Construction of Drain Purification Apparatus

| | irradiation part | | | | passed liquid | |
|---|---|---|---|---|---|---|
| | diameter mm | length mm | area cm$^2$ | volume cm$^3$ | passed liquid quantity ml/sec | residence time sec |
| [excimer lamp × 3] | 30 | 600 × 3 | 1700 | | | |
| double quartz flowing part inside diameter | 60 | 600 | | 610 | 10 | 60 |
| double quartz flowing part outside diameter | 70 | 600 | | | | |

EXAMPLE 9

Constructed was an excimer ultraviolet total reflection type raw water purification apparatus comprising an excimer ultraviolet lamp of a wavelength of a water-transmissive distance of several mm or more, concretely 2 mm or more, a quartz double tube, and a light reflection tube, wherein raw water containing organic matters was supplied inside the quartz double tube to purify the raw water by a photochemical reaction.

As the measurement result, the ability of decomposing TOC (total organic carbon concentration) in raw water to the maximum of 10 ppm was confirmed, like Example 8.

EXAMPLE 10

Constructed was an excimer ultraviolet total reflection type ozone gas supply apparatus comprising an excimer ultraviolet lamp of a wavelength of an air-transmissive distance of several mm or more, concretely 2 mm or more, a quartz double tube, and a light reflection tube, wherein air or air to which oxygen is added was supplied inside the quartz double tube to change oxygen into ozone by a photochemical reaction.

The excimer ultraviolet total reflection type apparatus shown in FIG. 2 and Table 11 was used, and as the excimer ultraviolet lamp, used was a Xe excimer ultraviolet lamp (wavelength of 172 nm: irradiation light quantity of 20 mJ/cm$^2$) whose in-air 50% transmissive distance is 3 mm.

By changing the irradiation light quantity of the excimer ultraviolet lamp by control of the applied quantity of electricity, the ozone concentration could be controlled within the range of 0 to about 7 vol. %.

quartz double tube to decompose organic matters and other contaminative components in the gas by a photochemical reaction.

The excimer ultraviolet total reflection type apparatus shown in FIG. 2 and Table 12 was used, and as the excimer ultraviolet lamp, used was a Xe excimer ultraviolet lamp (wavelength of 172 nm: irradiation light quantity of 20 mJ/cm$^2$) whose gas 50% transmissive distance is 10$^3$ mm or more.

Since the gas purification ability of this lamp can decompose and process about 40 mg/M$^3$ of organic matters by 20 mJ/cm$^2$ of irradiation light quantity, the light quantity is controlled in accordance with the organic matter concentration in the gas being processed.

Helium Gas Purification

In a system in which helium is circulated to an apparatus having need of a high-purity helium atmosphere, constructed was a helium gas purification apparatus for steadily and completely removing organic matter contamination in the atmosphere and organic matter contamination from pump/piping system of the circulation system. The helium gas purity was always monitored with an on-line type mass spectrometer (mass detection range 100). The purity of circulated helium could be kept less than 10 ppb that is the detection sensitivity to methane-conversion total organic matter concentration. A removal instrument for water and carbonic acid gas secondarily generated in organic matter decomposition is disposed together. In this apparatus, the ability of decomposing organic matters (oleic acid-conversion concentration) in gas to the maximum of 20 mg/M$^3$.

Purification of Other Gases

This apparatus could be used for purification of inert gas such as nitrogen, hydrogen, argon, and xenon, on quite the same conditions as those of helium purification.

TABLE 11

Construction of Ozone Gas Supply Apparatus

| | irradiation part | | | air supply | |
| --- | --- | --- | --- | --- | --- |
| | | | | flow | residence |
| | diameter mm | length mm | area cm$^2$ | volume cm$^3$ | rate ml/sec | time sec |
| [excimer lamp] | 30 | 300 | 282 | | | |
| double quartz flowing part inside diameter | 35 | 300 | | 190 | 2.5 | 76 |
| double quartz flowing part outside diameter | 40 | 300 | | | | |

EXAMPLE 11

Shown is an example of excimer ultraviolet total reflection type gas purification apparatus comprising an excimer ultraviolet lamp of a wavelength of a transmissive distance of several mm or more, concretely 2 mm or more, to each gas, a quartz double tube, and a light reflection tube, wherein atmospheric gas or material gas was supplied inside the

TABLE 12

Construction of Gas Purification Apparatus

| | irradiation part | | | | gas supply | |
| --- | --- | --- | --- | --- | --- | --- |
| | | | | | flow | residence |
| | diameter mm | length mm | area $cm^2$ | volume $cm^3$ | rate ml/sec | time sec |
| [excimer lamp] | 30 | 300 | 282 | | | |
| double quartz flowing part inside diameter | 35 | 300 | | 1200 | 1000 | 1.2 |
| double quartz flowing part outside diameter | 80 | 300 | | | | |

According to the present invention, an ultraviolet light reaction system is constructed for surface cleaning/surface processing, realization of a processing speed and an apparatus size that can not be attained by any conventional chemical reaction system, becomes possible, and it becomes possible to realize a time-sharing performance, a high-throughput performance, and a compact size.

What is claimed is:

1. An ultraviolet processing apparatus used purification of a surface and a material in relation to manufacturing a semiconductor device or a liquid crystal display device, comprising, as a light-source, an ultraviolet lamp for applying ultraviolet rays of a wavelength that have a 50% transmissive distance to air, water, steam, and a gas of 2 mm or more, respectively.

2. An ultraviolet processing apparatus described in claim 1, wherein said surface is one selected from among process surfaces from a substrate to a semiconductor device, surfaces of process apparatus and process apparatus parts, and surfaces of apparatus and apparatus parts in relation to lithographic processes.

3. An ultraviolet processing apparatus described in claim 1, wherein said material is one selected from among raw water, pure water, drain, general gases, and special material gases.

4. An ultraviolet processing apparatus described in claim 1, wherein said ultraviolet lamp is an excimer ultraviolet lamp.

5. An ultraviolet processing apparatus described in claim 1, wherein it is disposed in a surface purification apparatus using steam, and a surface being processed with steam is irradiated with ultraviolet rays that have a 50% transmissive distance to steam of 2 mm or more, in a superimposition manner with steam.

6. An ultraviolet processing apparatus described in claim 1, wherein it is disposed in a one-by-one surface purification apparatus, and a surface being processed with steam is irradiated with ultraviolet rays that have a 50% transmissive distance to steam of 2 mm or more, in a superimposition manner with steam to remove organic matters and adhering particles.

7. An ultraviolet processing apparatus described in claim 1, wherein it is disposed in a one-by-one surface purification apparatus, and a surface being cleaned with ultrapure water or a liquid chemical is irradiated with ultraviolet rays that 50% transmissive distance to air is 2 mm or more, to perform a radical reaction process.

8. An ultraviolet, processing apparatus described in claim 1, wherein it is disposed in a resist removal apparatus used in a lithographic process and a surface being processed with steam is irradiated with ultraviolet rays to remove a resist.

* * * * *